(12) United States Patent
Bartnik et al.

(10) Patent No.: US 8,000,779 B2
(45) Date of Patent: Aug. 16, 2011

(54) IMPEDANCE CARDIOGRAPHY SYSTEM AND METHOD

(75) Inventors: Daniel Bartnik, Eden Prairie, MN (US); Brandon Reynolds, Prior Lake, MN (US)

(73) Assignee: Vasamed, Inc., Eden Prairie, MN (US)

( * ) Notice: Subject to any disclaimer, the term of this patent is extended or adjusted under 35 U.S.C. 154(b) by 367 days.

(21) Appl. No.: 12/373,248

(22) PCT Filed: Sep. 7, 2007

(86) PCT No.: PCT/US2007/077882
§ 371 (c)(1),
(2), (4) Date: Jan. 9, 2009

(87) PCT Pub. No.: WO2008/031030
PCT Pub. Date: Mar. 13, 2008

(65) Prior Publication Data
US 2009/0292217 A1 Nov. 26, 2009

Related U.S. Application Data (60) Provisional application No. 60/824,869, filed on Sep. 7, 2006.

(51) Int. Cl.
*A61B 5/04* (2006.01)

(52) U.S. Cl. .................................................. 600/509
(58) Field of Classification Search ................... 600/509
See application file for complete search history.

(56) References Cited

U.S. PATENT DOCUMENTS

| | | | |
|---|---|---|---|
| 4,803,996 A | 2/1989 | Peel et al. | |
| 5,423,326 A | 6/1995 | Wang et al. | |
| 5,792,195 A | 8/1998 | Carlson et al. | |
| 6,156,154 A | * 12/2000 | McLeod et al. | .......... 156/345.42 |

FOREIGN PATENT DOCUMENTS

WO  WO 2005/008418  1/2005

\* cited by examiner

*Primary Examiner* — George Manuel
(74) *Attorney, Agent, or Firm* — Barbara A. Wrigley; Oppenheimer Wolff & Donnelly, LLP (57) ABSTRACT

An improved method and system for measuring and reporting heart valve activity combines information obtained from independent signals with information obtained from ICG signals, such that signals derived from heart valve activity may be used as confirmation that the ICG system is accurately identifying heart valve activity. The method and system of the present invention also provide improved accuracy in reported values such as PEP, LVET, STR, SV, and CO. In addition, the method and system of the present invention provide improved accuracy of graphical representations of heart activity where the graphical representations include identifying heart valve activity.

25 Claims, 8 Drawing Sheets

IMPEDANCE CARDIOGRAPHY SYSTEM AND METHOD

BACKGROUND OF THE INVENTION

1. Field of the Invention

The present invention relates to a method and system for measuring and reporting time based parameters associated with heart activity. More particularly, the present invention relates to a method and system for combining information gained from an independent signal with information gained from an impedance cardiography signal for monitoring and recording signals derived from heart valve activity.

2. Discussion of the Related Art

Impedance cardiography (ICG) is a technique used to provide non-invasive monitoring and analysis of a patient's cardiac performance. ICG systems measure and report several time-based parameters related to cardiac performance, including the pre-ejection period (PEP) and the left ventricular ejection time (LVET). ICG systems produce ICG signals from monitoring movement and volume of blood as a result of the heart contracting. Exemplary ICG systems are shown and described in Ackmann et al., U.S. Pat. No. 5,178,154; and Reining, U.S. Pat. No. 5,505,209 both incorporated by reference herein in their entireties. The '154 and '209 patents disclose the use of electrode bands placed on a patient with high frequency, low magnitude electrical current applied to the electrode bands. Voltage changes across the bands are read, filtered and converted into thoracic impedance. The ICG system displays the thoracic impedance signal versus time to create a visual display or ICG waveform. The '154 patent further discloses that ICG systems can receive conventional electrocardiograph signals, signals from blood pressure monitors, signals from piezoelectric microphones attached to the chest of the patient and the like. These signals, in addition to thoracic impedance, can be stored and averaged via a memory storage device connected to the ICG system.

Phonocardiography (PCG) is a non-invasive technique used by healthcare professionals to monitor cardiac performance. PCG systems use a microphone that records sounds of heart valve activity, similar to electronic stethoscopes known in the art, in order to provide signals of acoustic events emanating from the heart. Analysis of signals recorded by PCG systems can be used to identify aortic valve opening (shown as S1 on FIG. 1) and aortic valve closing (shown as S2 on FIG. 1) of valves within a patient's heart.

Echocardiography (ECG) is another non-invasive system used to monitor heart activity. ECG uses a transducer to direct ultrasound waves into a patient's chest to produce an image of the heart muscle and heart valves. The transducer, also called a probe, is a small handheld device at the end of a flexible cable. The transducer, essentially a modified microphone, is placed against the chest and directs ultrasound waves into the chest such that some of the waves get echoed (or reflected) back to the transducer. Since different tissues and blood reflect ultrasound waves differently, these sound waves can be translated into a meaningful image of the heart that can be displayed on a monitor or recorded on paper or tape.

Still another non-invasive system used by healthcare professionals to monitor cardiac performance is a blood pressure system. A patient's blood pressure is monitored according to known techniques and converted into a blood pressure signal. The blood pressure signal is then displayed on a blood pressure waveform. Blood pressure waveforms, similar to PCG waveforms, can be used by healthcare professionals to identify heart valve closure because the dicrotic notch in blood pressure waveforms reflects closure of the aortic heart valve.

Other exemplary systems using signals that have pulsatile characteristics resulting from the contraction of the heart are shown and described in Kimball et al., U.S. Pat. No. 6,763,256, herein incorporated by reference in its entirety.

The PEP is defined as the period of isovolumic ventricular contraction when the patient's heart is pumping against the closed aortic valve. In ICG systems, the PEP is measured starting with the initiation of the QRS complex (the "Q" point on FIG. 1) of the ECG signal and ending with the start of the mechanical systole as marked by the initial deflection of the systolic waveform (the "B" point on FIG. 1) of the ECG signal coincident with the opening of the aortic valve or the onset of left ventricular ejection into the aorta. The LVET begins at the end of the PEP and ends at the closure of the aortic valve (the "X" Point on FIG. 1) when ejections ends.

It is important that ICG systems provide accurate results for the PEP and the LVET because healthcare professionals utilize the results of these parameters when making decisions about patient diagnosis and care. Additionally, accurate determination of the PEP and the LVET time intervals is also required for accurate and reliable determination of subsequent and dependent parameters. For example, results from determination of the PEP and the LVET are used to calculate the systolic time ratio (STR), where STR=PEP/LVET. While many ICG systems use proprietary equations for determination of stroke volume (SV), it is commonly known that SV equations frequently incorporate LVET as an input parameter. Accordingly, accurate determination of time intervals between the PEP and the LVET is also necessary for accurate determination of SV, and subsequently for cardiac output (CO) based on SV and heart rate (HR), where CO=SV*HR.

Many ICG waveforms, particularly for healthy individuals, provide sufficient detail so that healthcare professionals can identify the location of the aortic valve opening and closing, or the LVET, with a high degree of confidence. For example, in the ICG waveform 10 depicted in FIG. 1, opening, B point, of the aortic valve and closing, X point, of the aortic valve are easily identifiable. When comparing the ICG waveform 10 with the phonocardiograph (PCG) waveform 12 (both shown in FIG. 1), marking of the B point in the ICG waveform 10 is confirmed by the time-associated presence of the S1 component in the PCG waveform 12. Similarly, marking of the X point in the ICG waveform 10 is confirmed by the time associated presence of the S2 component in the PCG waveform 12.

Figure 2:
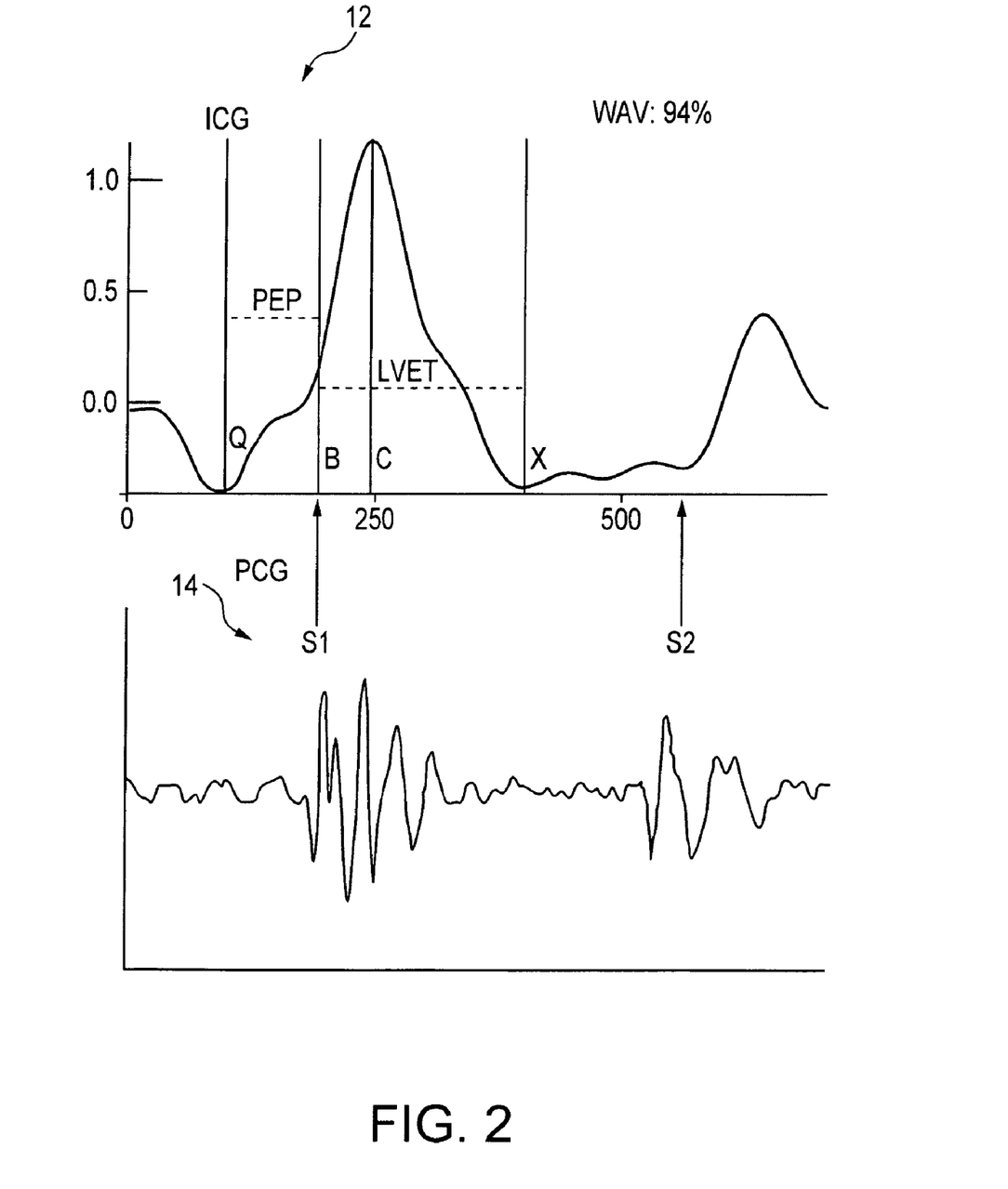
FIG. 2 represents ICG and PCG waveforms of a patient with difficult to recognize heart valve activity.

Traditionally, ICG systems only analyze attributes of the impedance signal when determining the location of heart valve activity. Some ICG systems may record and display PCG signals, blood pressure signals, and/or other signals having pulsatile characteristics resulting from contraction of the heart, but these ICG systems do not integrate the signals into an automatic location of heart valve activity. ICG systems alone often lack sufficient information for healthcare professionals to accurately and reliably determine the PEP and the LVET because of confounding information related to opening and closing of the patient's aortic valve. For example, in the ICG waveform 10 depicted in FIG. 2, closure, X point, of the aortic valve could be any of several depressions following the peak blood flow, C. The known algorithm selected the deepest depression in the ICG waveform 10 because the aortic valve closure is often thought to produce the strongest negative signal. However, when the ICG waveform 10 depicted in FIG. 2 is compared with the PCG waveform 12 depicted in FIG. 2, the aortic valve closure, X point, should have been one of the later depressions in the ICG waveform 10 in order to correlate with the time associated presence of the S2 component in the PCG waveform 12.

Accordingly, there is a need for a method and system for measuring and reporting time based parameters associated with heart activity that correlates impedance signals from ICG systems with independent signals derived from heart valve activity in order to provide more accurate identification of heart valve activity.

It is known that experienced healthcare professionals can recognize, or diagnose, certain disease states by analyzing hemodynamic parameters and ICG waveforms provided by some ICG systems. Experienced healthcare professionals can easily recognize the systolic and diastolic segments of ICG waveforms in addition to other attributes of the waveform, such as amplitude, shape, tone, slope and timing, in combination with hemodynamic parameters. Analysis of these attributes allows experienced healthcare professionals to ascertain an underlying disease state.

It is also known that some ICG systems provide minimal ICG waveform information. When using these types of systems, healthcare professionals must rely largely on numeric parameters to make a diagnosis because these systems do not provide other information. With ICG systems that display waveforms but provide them individually, experienced healthcare professionals may still be unable to analyze all waveform attributes and relationships to make a diagnosis. Accordingly, there exists a need for an improved method for displaying ICG waveform information in combination with information obtained from independent signals.

Based on the foregoing, there exists a need for a method and system that provides better identification of heart valve activity when measuring cardiac function within an ICG system. There also exists a need for method and system for measuring and reporting time based parameters associated with heart activity that correlates impedance signals from ICG systems with independent signals derived from heart valve activity in order to provide more accurate identification of heart valve activity. There exists yet another need for an improved method for displaying waveform information in combination with information obtained from independent signals.

SUMMARY OF THE INVENTION

It is one object of the present invention to provide an improved method and system for measuring and reporting heart valve activity by combining information obtained from independent signals with information obtained from ICG signals, such that the signals derived from heart valve activity are used as confirmation that the ICG system is accurately identifying heart valve activity. It is a second object of the present invention to provide improved accuracy in reported values such as PEP, LVET, STR, SV and CO. It is a third object of the present invention to provide improved accuracy of graphic presentation of heart activity where the graphic presentation includes identifying heart valve activity.

These and other objects and advantages of the present invention are accomplished by the improved impedance cardiography method and system in accordance with the present invention. The invention will be further described with reference to the following detailed description taken in conjunction with the drawings.

DETAILED DESCRIPTION

Figure 1:
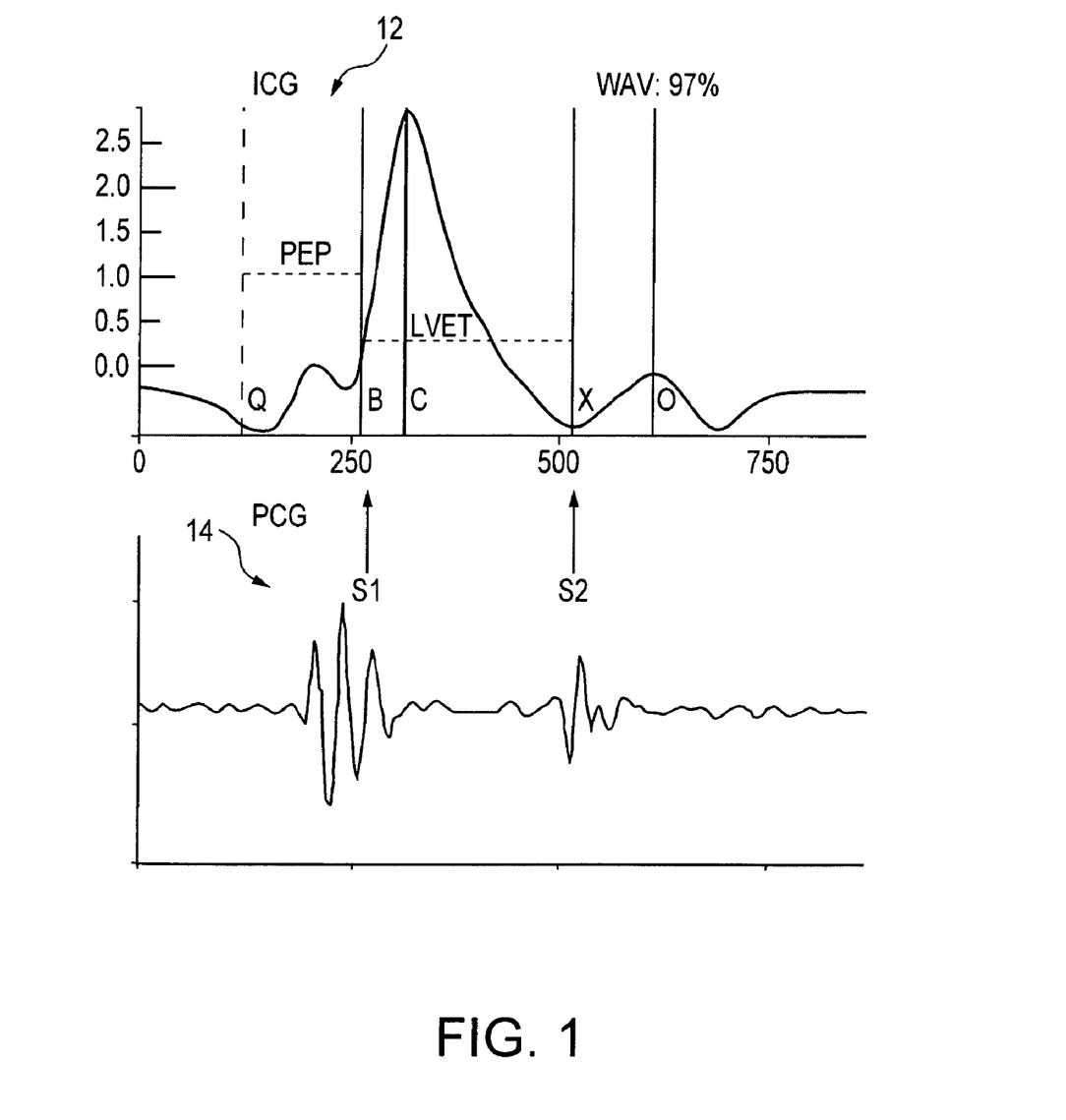
FIG. 1 represents ICG and PCG waveforms of a patient with easily recognizable heart valve activity.

Referring to FIGS. 1 and 2, there is shown an ICG waveform 10 and a PCG waveform 12 in accordance with the system and method of the present invention. Both figures depict heart valve activity in ICG waveform 10. The PEP is determined by identifying the time period between the starting point of the QRS complex based on an ECG signal, labeled as the Q point, and the starting point of the mechanical systole as marked by the initial deflection of the systolic waveform based on the ICG signal coincident with the opening of the aortic valve or the onset of left ventricular ejection into the aorta, labeled as the B point. The LVET is determined by identifying the time period between the end of the PEP and the closure of the aortic valve when ejection ends, labeled as the X point. Both figures also depict heart valve activity in PCG waveform 12, where known devices and methods are used to monitor and record sounds associated with the aortic valve opening, labeled as S1, and closing, labeled as S2. While FIGS. 1 and 2 depict PCG waveforms 12, those skilled in the art can appreciate that waveforms generated from any independent signals derived from heart valve activity can be depicted in relation to ICG waveforms 10.

Figure 3:
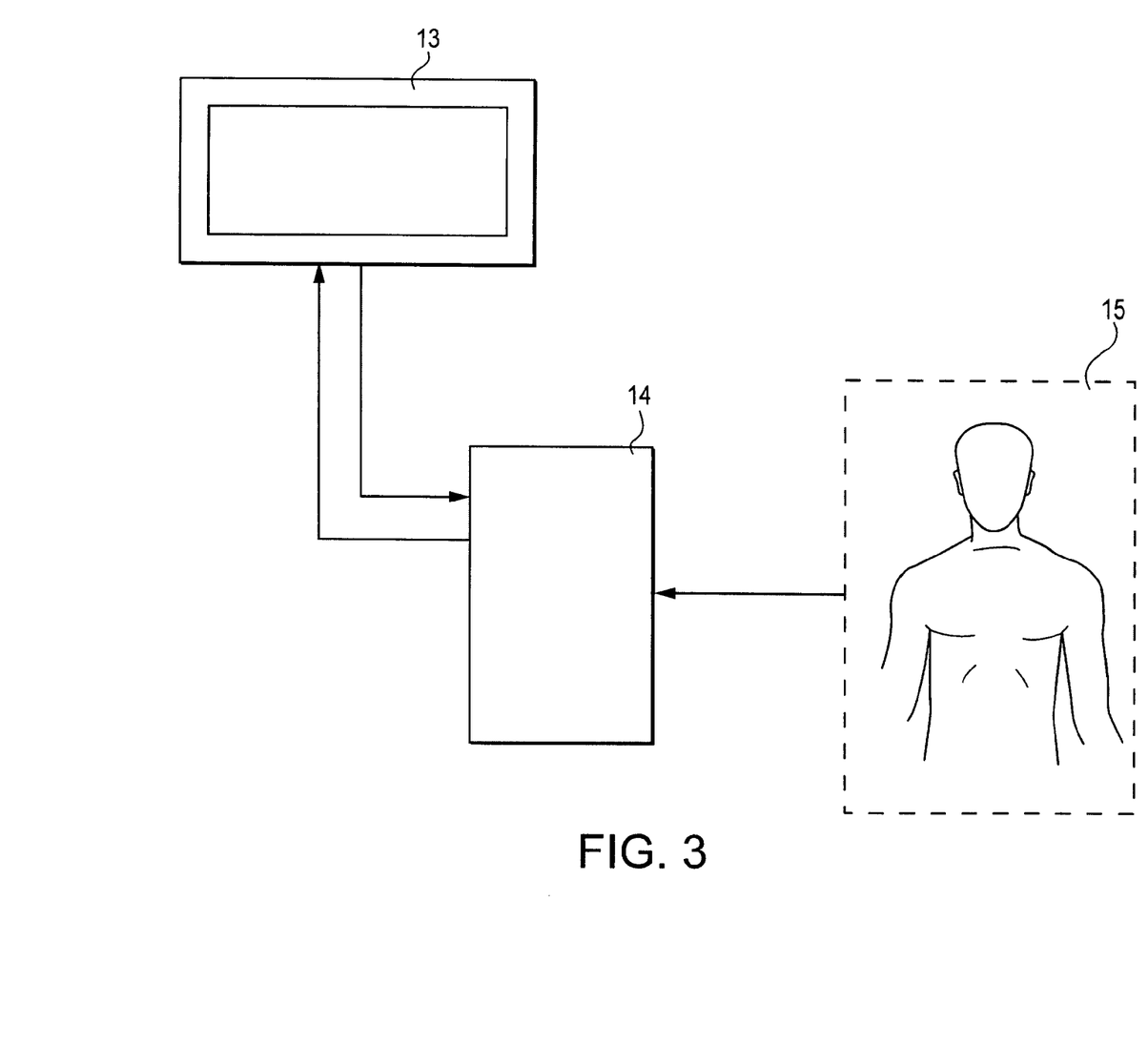
FIG. 3 is an exemplary schematic diagram of one embodiment of the system of the present invention illustrating the principal components thereof.

Referring to FIG. 3, one embodiment of the system in accordance with the present invention includes a display device 13 used to display waveforms and a processing device 14 used to receive inputs from a sensor system 15 hooked to a patient in order to generate waveforms and communicate with display device 13. Those skilled in the art can appreciate that display device 13 may include any type of device for presenting visual information such as, for example, a computer monitor or flat-screen display. Display device 13 may be equipped with user input devices, such as buttons or touch screen capabilities for enabling user input, operation and control of the system. Those skilled in the art can also appreciate that sensor system 15 may include electrodes for measuring ICG signals and ECG signals, microphones for measuring and recording heart sounds, blood pressure monitors, signals representing central venous pressure, finger plethysmographs and the like. Those skilled in the art will appreciate that the system in accordance with the present invention may include stationary systems used in intensive care units or emergency rooms in hospitals, or may comprise portable units for use by emergency medical technicians in ambulances, at the scene of accidents, and when responding to other emergency situations.

Figure 4:
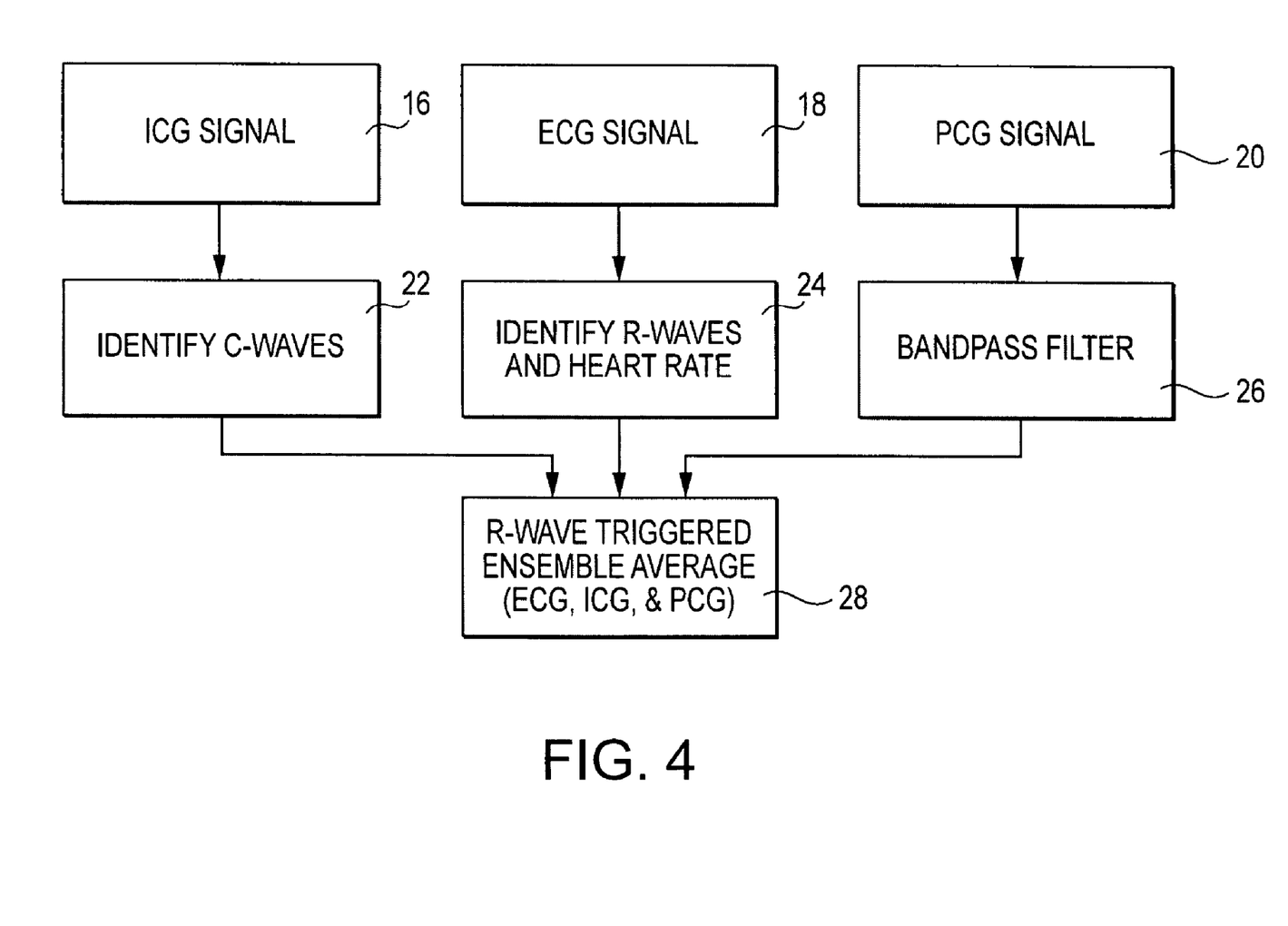
FIG. 4 is a flowchart illustrating one embodiment for deriving an ensemble average.
Figure 5:
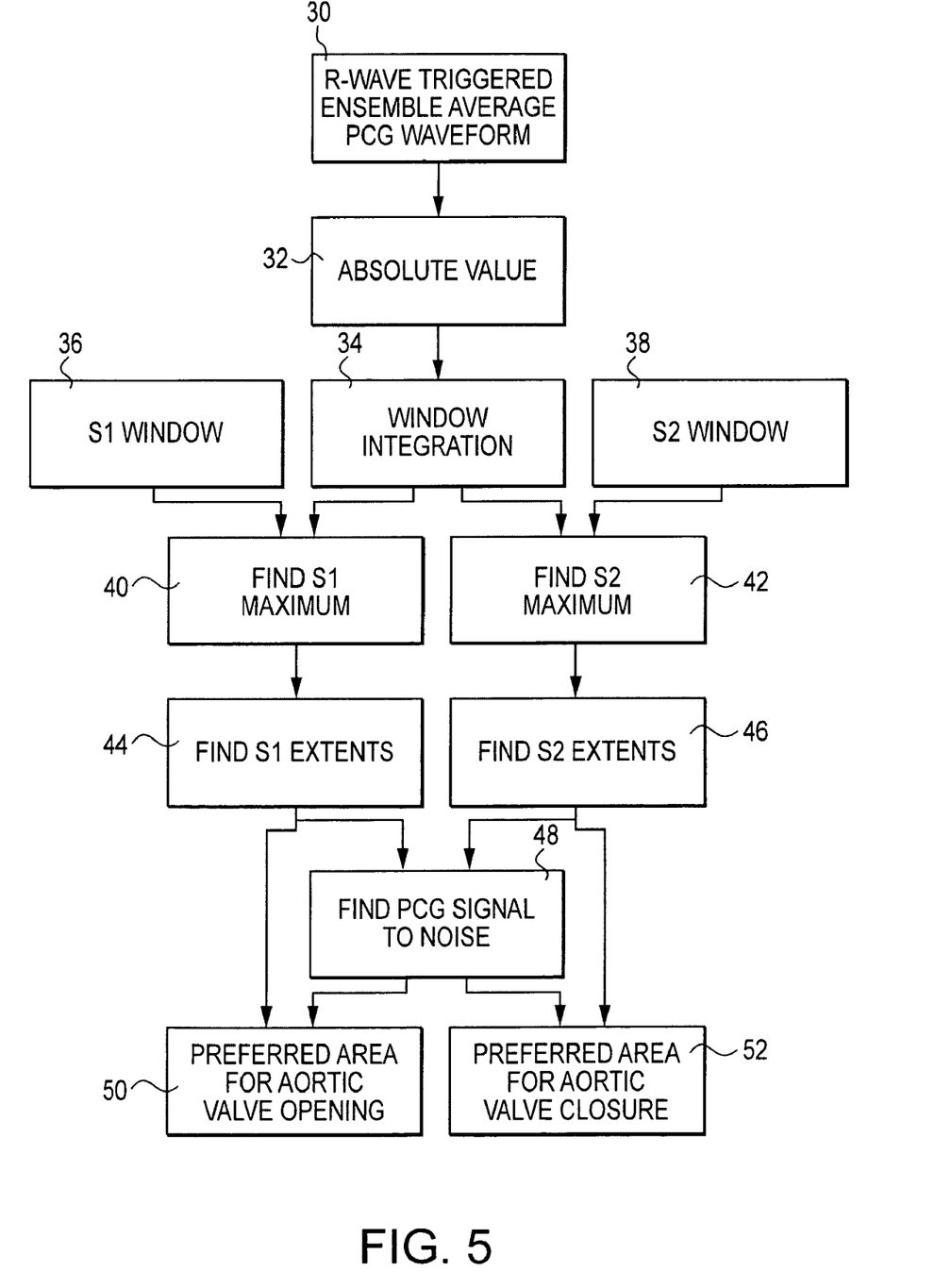
FIG. 5 is a flowchart illustrating one embodiment for determination of likely valve activity.
Figure 6:
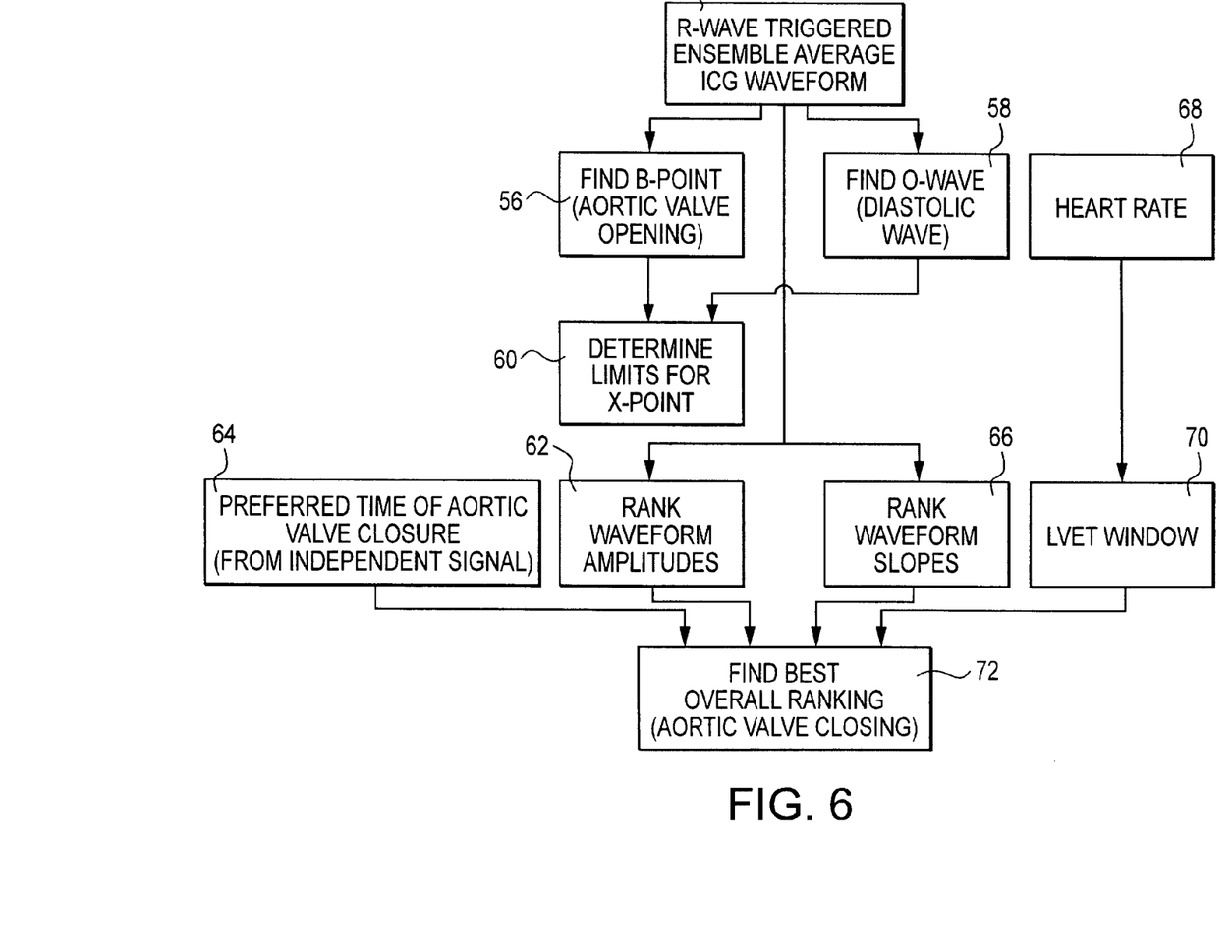
FIG. 6 is a flowchart illustrating one embodiment for identifying aortic valve closing point.

In another embodiment in accordance with the present invention, independent signals can be produced from one or more means that are sensitive to heart valve activity. Sources of the independent signals include but are not limited to PCG's, blood pressure waveforms, heart sounds, ECG's or user input. In one embodiment, an algorithm based on an empirical, mathematical model can be used to combine information from independent signals with information from ICG signals to determine heart valve activity and placement of the same on waveforms. The algorithm can include a set of coefficients, such as probability coefficients, applied to recent values of the differences between the ICG signals and the independent signals derived from heart valve activity in order to provide accurate weight to input signals being received by a processing device (such as a computer processor) in order to generate accurate graphic representations depicting heart valve activity. These coefficients can be multiplied by a sensitivity factor based on individual sensor errors, system errors or historic errors in correlating ICG signals with independent signals derived from heart valve activity for a particular patient. In this manner, sensor and system errors can be accounted for when modifying ICG waveforms based on independent signals derived from heart valve activity. FIGS. 4 through 6 depict embodiments in accordance with the present invention in which information generated from independent signals can be depicted in relation to ICG waveforms.

Referring to FIG. 4, one embodiment of a method for deriving an ensemble average in accordance with the present invention includes steps for: inputting an ICG signal 16; inputting an ECG signal 18; inputting a PCG signal 20; identifying C-waves from the ICG signal 22; identifying R-waves and heart rate from the ECG signal 24; filtering the PCG signal through a bandpass filter 26; and deriving an R-wave triggered ensemble average 28. While FIG. 4 depicts inputting signals from an ICG, an ECG and a PCG, those skilled in the art can appreciate that input signals can be derived from other sources as previously discussed, manipulated, and combined with other input signals to derive an ensemble average that can be used to determine proper placement of heart valve activity on a graphic representation, such as a waveform or a combined waveform.

Referring now to FIG. 5, one embodiment for a method of determining preferred areas for aortic valve opening and closing in accordance with the present invention includes the steps of: inputting an R-wave triggered ensemble average PCG waveform 30; deriving an absolute value 32; calculating a window integration 34; inputting an S1, or aortic valve opening, window 36; inputting an S2, or aortic valve closure, window 38; determining an S1 maximum 40; determining an S2 maximum 42; determining an S1 extent 44; determining an S2 extent 46; determining a preferred area to be identified as the aortic valve opening point on a graphic representation 50; and determining a preferred area to be identified as the aortic valve closure point on a graphic representation 52. In one embodiment, the S1 and S2 extent values can be used to find a value for PCG signal to noise 48. The value for PCG signal to noise can be used to determine preferred areas to be identified as the aortic valve closure and opening points on the graphic representation. While FIG. 5 depicts an embodiment for determining aortic valve opening and closure points on a graphic representation starting with an R-wave triggered ensemble average PCG waveform, those skilled in the art can appreciate that the input PCG signal could be pre-processed in manners other than ensemble averaging, including but not limited to the input PCG signal being a raw unprocessed signal or a signal from an independent source other than PCG that can be used to derive aortic valve opening and closing points and/or other heart valve activity that can be depicted graphically in combination with ICG waveforms. Examples of other independent source signals are echocardiography, blood pressure, and the like.

As illustrated in the flowchart depicted in FIG. 6, one method for determining the best overall rank for aortic valve closing point on the graphic representation includes the steps of: inputting an R-wave triggered ensemble average ICG waveform 54; finding the B point, which represents the opening of the aortic valve or the onset of left ventricular ejection into the aorta, 56; finding the O-wave, which represents the diastolic segment of the ICG waveform, 58; determining limits for the X-point using the B-point and the O-wave as inputs 60; ranking waveform amplitudes 62; ranking waveform slopes 66; utilizing a preferred time of aortic valve closure as determined from the signal of an independent source 64; utilizing heart rate as determined from ECG or other signal 68; determining a window for the LVET using the heart rate as an input 70; and finding the best overall ranking for the aortic valve closing 72. In this embodiment, steps for ranking waveform amplitudes 62, ranking waveform slopes 66, utilizing a preferred time of aortic valve closure as determined from the signal of an independent source 64, and utilizing heart rate as determined from ECG or other signal 68 are conducted before and utilized to find the best overall ranking for the aortic valve closing 72. Those skilled in the art can appreciate that steps 62, 66, 64 and 68 can be conducted in varying orders or simultaneously. While FIG. 6 depicts a method for finding the best overall ranking for graphically representing aortic valve closure using an R-wave triggered ensemble average ICG waveform, those skilled in the art can appreciate that the input PCG signal can be pre-processed in manners other than ensemble averaging, including but not limited to using a raw unprocessed signal or a signal from an independent source other than PCG that can be used to derive aortic valve opening and closing points, and/or other heart valve activity that can be depicted graphically in combination with ICG waveforms.

Figure 7:
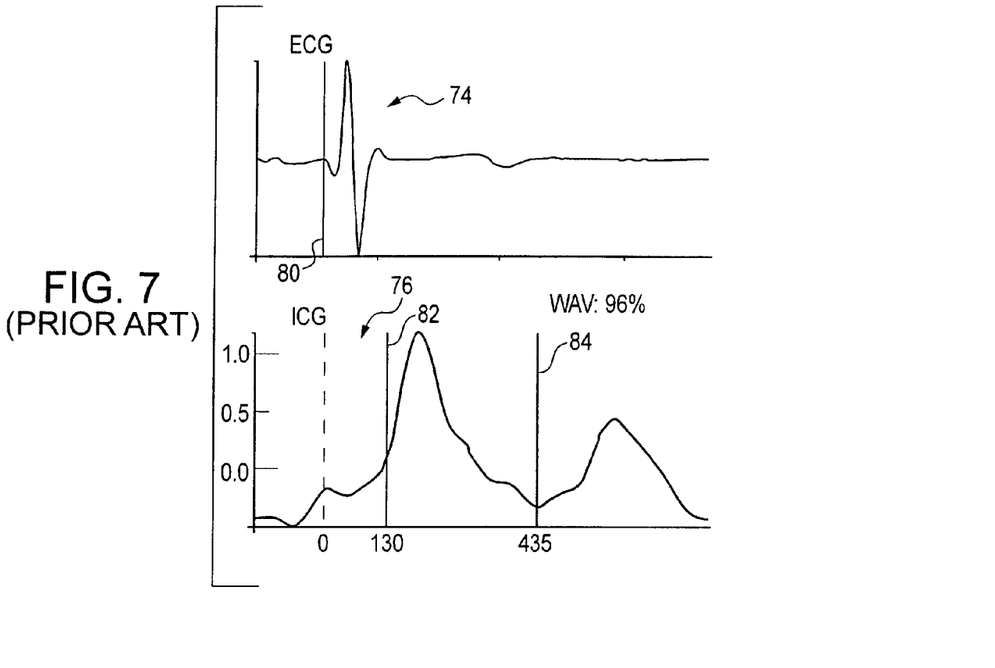
FIG. 7 represents a traditional graphic representation of an ICG waveform and an ECG waveform.
Figure 8:
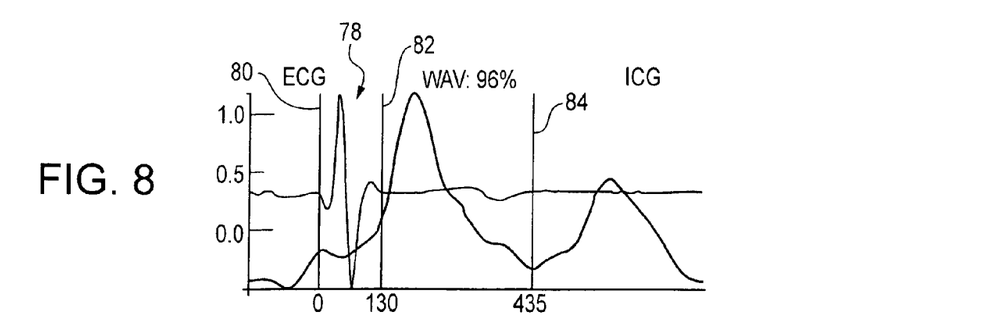
FIG. 8 represents a graphic representation of a combined waveform, or single overlay graph.

Referring now to FIGS. 7 and 8, an alternate embodiment in accordance with the present invention provides a method for displaying waveforms. According to the prior art as depicted in FIG. 7, ECG waveforms 74 and ICG waveforms 76 are traditionally viewed separate from one another. FIG. 8 depicts a new method for displaying waveforms in according to the present invention where ICG waveforms 76 are combined with ECG waveforms 74 on a single overlay graph 78 such that users can obtain greater utility from the combined waveform than can be obtained by viewing the two waveforms individually. The increase in utility is a result of both ECG waveforms 74 and ICG waveforms 76 depicting systolic time interval characteristics. For example, the onset of PEP is typically obtained from the Q-point of the ECG signal and the end of the PEP is typically obtained form the upward portion of the ICG signal in ICG systems. Waveforms depicting a combined graphical representation of the systolic intervals, such as the PEP and the LVET, convey information to users more efficiently than separate waveforms.

Single overlay graph 78 also assists users in identifying the diastolic interval. The key points of the systolic time interval are marked by vertical lines 80, 82, 84 in FIGS. 6 and 7. Line 80 marks the onset of the PEP and is determined by the Q-point of the ECG. Line 82 marks the end of the PEP and the start of the LVET and is determined by the ICG signal. Line 82 can optionally be determined via one or a combination of more than one the aforementioned independent signals, which can include the ICG signal. Line 84 marks the end of the LVET and is determined by the ICG signal. Line 84 can also optionally be determined via one or a combination of more than one of the aforementioned independent signals, which can include the ICG signal.

While the waveforms depicted in FIGS. 7 and 8 are ICG and ECG waveforms 74, 76, those skilled in the art can recognize that this method may be used on any type of waveform. Those skilled in the art can also recognize that this method may be used with graphic representations that correlate ICG signals with any signals measured, derived from or related to cardiac sources, and any other combination thereof.

Figure 9:
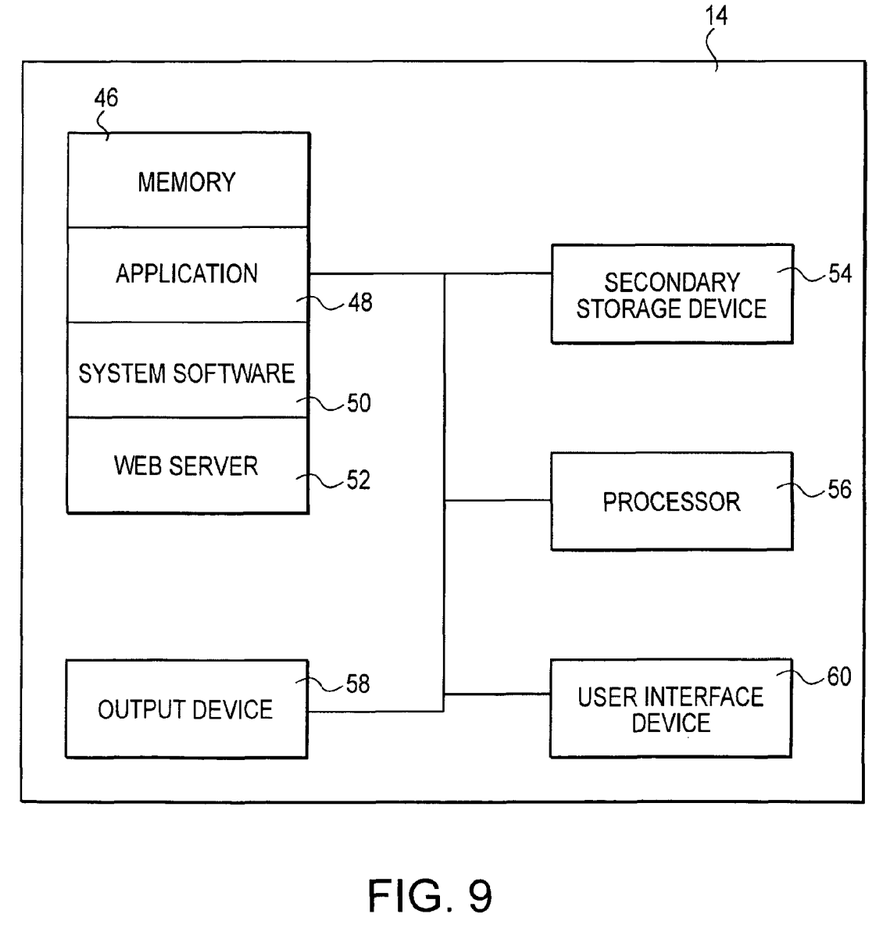
FIG. 9 is a block diagram of the exemplary components of an electronic processing device used in accordance with the system of the present invention.

Referring now to FIG. 9, processing device 14 illustrates typical components of a processing device. Processing device 14 includes a local memory 86, a secondary storage device 94, a processor 96, a user interface device 100 and an output device 98. Local memory 86 may include random access memory (RAM) or similar types of memory, and it may store one or more applications 88, including system software 90, and a web server 92, for execution by processor 96. Local memory 86 is generally located in individual pieces of equipment used to monitor cardiac performance of patients. Secondary storage device 94 may include a hard disk drive, floppy disk drive, CD-ROM drive, or other types of nonvolatile data storage. The local cache that includes a patient's waveform and heart valve activity data may be stored on secondary storage device 94. Processor 96 may execute system software 90 and other applications 88 stored in local memory 86 or secondary storage 94. Processor 96 may execute system software 90 in order to provide the functions described in this specification including measuring, reporting and displaying individual and/or combined waveforms with or without other graphic representations of heart valve activity. User interface device 100 may include any device for entering information into processing device 14, such as a keyboard, mouse, cursor-control device, touch-screen, infrared, microphone, digital camera, video recorder, or any other instrument or device necessary to measure, report and display individual and/or combined waveforms with or without other graphic representations of heart valve activity. Output device 98 may include any type of device for presenting a hard copy of information, such as a printer, and other types of output devices include speakers or any device for providing information in audio form.

Web server 92 is used to provide access to patient data stored in memory 86 and on secondary storage devices 94 and display the data. Web server 92 allows users secure remote access to the system through which they can monitor the status of a patient's cardiovasculograms and access patient data. Web server 92 can allow access to a user running a web browser. Examples of web browsers include the Netscape Navigator program and the Microsoft Internet Explorer program. Any web browser, co-browser, or other application capable of retrieving content from a network and displaying pages or screens may be used.

Examples of processing devices 14 for interacting within the system for measuring and displaying individual or combined waveforms with or without graphic representation of other valve activity include embedded microprocessors, digital signal processors, personal computers, laptop computers, notebook computers, palm top computers, network computers, Internet appliances, or any processor-controlled device capable of storing data, system software 90 and any other type of application 88 stored in local memory 86 or accessible via secondary storage device 94.

While the invention has been described with reference to the specific embodiments thereof, those skilled in the art will be able to make various modifications to the described embodiments of the invention without departing from the true spirit and scope of the invention. The terms and descriptions used herein are set forth by way of illustration only and are not meant as limitations. Those skilled in the art will recognize that these and other variations are possible within the spirit and scope of the invention as defined in the following claims and their equivalents.

We claim:

1. A method for displaying waveforms comprising:
    inputting a first waveform;
    inputting a second waveform;
    overlaying the second waveform on the first waveform to form a combined waveform, the combined waveform depicting systolic time interval characteristics; and
    outputting the combined waveform onto a display.

2. The method of claim 1, wherein the first waveform is an impedance cardiography (ICG) waveform.

3. The method of claim 2, wherein the second waveform is an echocardiography (ECG) waveform.

4. The method of claim 3, further comprising the step of identifying a pre-ejection period (PEP) based upon the combined waveform.

5. The method of claim 3, further comprising the step of identifying a left ventricular ejection time (LVET) based upon the combined waveform.

6. The method of claim 1, further comprising the step of identifying heart valve activity based upon the combined waveform.

7. The method of claim 1, wherein the first waveform represents a thoracic impedance signal over a period of time.

8. The method of claim 7, wherein the second waveform represents a time based parameter associated with heart activity.

9. The method of claim 8, wherein the second waveform is generated from an independent signal derived from heart valve activity.

10. A cardiography system for determining time based parameters associated with heart valve activity comprising:
    a sensor system adapted to provide a first signal and a second signal;
    a processing device operably coupled to the sensor system and configured to receive the first and second signals;
    a display operably coupled to the processing device and configured to display a first waveform generated from the first signal and one or more graphical points generated from the second signal;
    wherein the first waveform and the one or more graphical points are combined on a single overlay graph on the display in order to identify heart valve activity.

11. The cardiography system of claim 10, wherein the first waveform is an impedance cardiography (ICG) waveform.

12. The cardiography system of claim 10, wherein the one or more graphical points generated from the second signal comprise a second waveform.

13. The cardiography system of claim 12, wherein the second waveform is an echocardiography (ECG) waveform.

14. The cardiography system of claim 10, wherein the first signal is an impedance cardiography (ICG) signal.

15. The cardiography system of claim 14, wherein the second signal is an independent signal generated by one or more means that are sensitive to heart valve activity.

16. The cardiography system of claim 15, wherein the processing device combines information from the independent signal with the ICG signal to identify heart valve activity.

17. The cardiography system of claim 16, wherein a visual indication of the heart valve activity is displayed on the display.

18. The cardiography system of claim 16, wherein the information from the independent signal and the ICG signal is combined by the processing device in order to derive a modified ICG waveform.

19. The cardiography system of claim 10, wherein the sensor system comprises one or more electrodes for measuring signals.

20. The cardiography system of claim 10, further comprising an input device adapted for receiving manual user input.

21. The cardiography system of claim 10, further comprising a storage device for storing heart valve activity data.

22. A method for determining an ensemble average for use in identifying heart valve activity on a graphic waveform comprising:
propagating an impedance cardiography (ICG) signal;
propagating an echocardiography (ECG) signal;
propagating a phonocardiography (PCG) signal;
identifying C-waves from the ICG signal;
identifying R-waves and heart rate from the ECG signal;
filtering the PCG signal through a bandpass filter; and
deriving an R-wave triggered ensemble average.

23. A method for determining aortic valve opening and closing points comprising:
inputting a waveform derived from an independent signal representing heart valve activity;
deriving an absolute value of the waveform;
calculating a window integration of the waveform;
inputting an aortic valve opening window;
inputting an aortic valve closing window;
determining an aortic valve opening maximum;
determining an aortic valve closing maximum;
determining an aortic valve opening extent;
determining an aortic valve closing extent;
deriving a preferred area to be identified as an aortic valve opening point on a graphical representation in combination with an impedance cardiography (ICG) waveform; and
deriving a preferred area to be identified as an aortic valve closing point on the graphical representation in combination with the ICG waveform.

24. The method of claim 23, wherein the waveform derived from an independent signal comprises a phonocardiography (PCG) waveform.

25. The method of claim 24, wherein the PCG waveform is an R-wave triggered ensemble average PCG waveform.

* * * * *